United States Patent
Windecker et al.

(10) Patent No.: US 8,476,463 B2
(45) Date of Patent: Jul. 2, 2013

(54) PROCESS FOR SEPARATING OFF FUMARIC ACID AND OTHER MINOR COMPONENTS DURING THE PRODUCTION OF MALEIC ANHYDRIDE

(75) Inventors: Gunther Windecker, Ludwigshafen (DE); Jens Weiguny, Freinsheim (DE); Alexander Weck, Freinsheim (DE); Ellen Dahlhoff, Limburgerhof (DE); Wolf-Steffen Weißker, Lambsheim (DE); Jörg Heilek, Bammental (DE); Thomas Krug, Worms (DE); Ralf Freyberger, Shanghai (CN)

(73) Assignee: BASF SE (DE)

( * ) Notice: Subject to any disclaimer, the term of this patent is extended or adjusted under 35 U.S.C. 154(b) by 294 days.

(21) Appl. No.: 12/935,894

(22) PCT Filed: Mar. 23, 2009

(86) PCT No.: PCT/EP2009/053338
§ 371 (c)(1), (2), (4) Date: Sep. 30, 2010

(87) PCT Pub. No.: WO2009/121735
PCT Pub. Date: Oct. 8, 2009

(65) Prior Publication Data
US 2011/0021789 A1    Jan. 27, 2011

(30) Foreign Application Priority Data
Apr. 1, 2008 (EP) .................................. 08153909

(51) Int. Cl.
*C07D 307/36* (2006.01)
*C07D 307/34* (2006.01)

(52) U.S. Cl.
USPC .......................... 549/262; 549/258

(58) Field of Classification Search
USPC ................................ 549/258, 262
See application file for complete search history.

(56) References Cited

U.S. PATENT DOCUMENTS

| 4,118,403 A | 10/1978 | White |
| 5,929,255 A * | 7/1999 | Forgac .................... 549/258 |
| 2009/0143601 A1 | 6/2009 | Pinkos et al. |

FOREIGN PATENT DOCUMENTS

| DE | 102006024903 A1 | 11/2007 |
| WO | WO-96/29323 A1 | 9/1996 |

OTHER PUBLICATIONS

Lohbeck, K., et al., "Maleic and Fumaric Acids," Ullmann's Encyclopedia of Industrial Chemistry, 2005, Wiley-VCH-Verlag GmbH & Co KGaA, Weinheim.

*Primary Examiner* — Taylor Victor Oh
(74) *Attorney, Agent, or Firm* — Novak Druce Connolly Bove + Quigg LLP

(57) ABSTRACT

Processes for decreasing fumaric acid deposits in preparing maleic anhydride by heterogeneously catalyzed oxidation of a hydrocarbon with molecular oxygen. Maleic anhydride is absorbed from the crude mixture in an absorbent in an absorption column and desorbed in a desorption column, the entirety or portion of absorbent depleted in maleic anhydride, for controlled precipitation of fumaric acid, being cooled and/or concentrated by evaporating a portion of absorbent such that the difference between the concentration of fumaric acid in the recycle stream at the outlet of the desorption column under existing conditions and the equilibrium concentration of fumaric acid according to the solubility curve after cooling and/or evaporation of a portion of absorbent is ≧250 ppm by weight, and the fumaric acid precipitated as a solid is removed completely or partly from the absorbent recycling system and the fumaric acid-depleted absorbent is recycled completely or partly to the absorption column.

11 Claims, 3 Drawing Sheets

Fig. 2: Schematic plot of the fumaric acid concentration in theoretical example 1

PROCESS FOR SEPARATING OFF FUMARIC ACID AND OTHER MINOR COMPONENTS DURING THE PRODUCTION OF MALEIC ANHYDRIDE

CROSS-REFERENCE TO RELATED APPLICATIONS

This application is a national stage application (under 35 U.S.C. §371) of PCT/EP2009/053338, filed Mar. 23, 2009, which claims benefit of European application 08153909.1, filed Apr. 1, 2008, the contents of each of which are incorporated herein by reference in their entireties.

FIELD OF THE INVENTION

The present invention relates to a process for decreasing fumaric acid deposits in the preparation of maleic anhydride by heterogeneously catalyzed oxidation of a hydrocarbon selected from the group of benzene, n-butane, n-butene and 1,3-butadiene with molecular oxygen in the presence of a catalyst comprising vanadium, phosphorus and oxygen, comprising
(a) the absorption of maleic anhydride from the crude product mixture in an absorbent comprising an organic solvent in an absorption column;
(b) the desorption of the maleic anhydride from the maleic anhydride-enriched absorbent obtained in step (a) in a desorption column; and
(c) the full or partial recycling of the absorbent depleted of maleic anhydride in step (b) to step (a).

The process according to the invention serves to improve the industrial scale preparation of maleic anhydride. Maleic anhydride is an important intermediate in the synthesis of γ-butyrolactone, tetrahydrofuran and 1,4-butanediol, which are themselves used as solvents or are processed further, for example, to give polymers such as polytetrahydrofuran or polyvinylpyrrolidone.

BACKGROUND OF THE INVENTION

Maleic anhydride can be obtained by partial oxidation of hydrocarbons, especially benzene or $C_4$-hydrocarbons, such as 1,3-butadiene, n-butene or n-butane. The reaction is strongly exothermic and requires sufficient removal of the heat of reaction. In general, the reaction is carried out in a tube bundle reactor with a salt circulation system or a fluidized bed. The maleic anhydride formed in the reaction is typically absorbed from the crude product mixture formed in a solvent. This absorbs not only maleic anhydride but also further components present in the crude product mixture, for example including the water formed in the oxidation. The water reacts partly with the maleic anhydride to give maleic acid, which in turn isomerizes partly to fumaric acid. Fumaric acid is a dicarboxylic acid which has very sparing solubility in water or organic solvents, forms deposits and as a result can block plant parts, for example columns, heat exchangers, pumps, pipes and the like.

There are already some proposals in the prior art for preventing such blockages caused by fumaric acid.

For instance, WO 96/029,323 describes washing the fumaric acid-comprising absorbent, after stripping out maleic anhydride, with an aqueous extractant in order thus to prevent deposits. A disadvantage of this process is the high level of complexity which is needed to mix the washing water into an industrial scale system for preparing $C_4$-dicarboxylic acids or derivatives thereof and to separate the phases again. In addition, the unavoidable loss of valuable product and solvent causes high costs. Moreover, the additional introduction of water into the process enhances fumaric acid formation further.

DE-10 2006 024 903.8 proposes completely or partly catalytically hydrogenating the fumaric acid-comprising absorbent after stripping out maleic anhydride, and recycling it completely or partly into the absorption stage.

BRIEF SUMMARY OF THE INVENTION

Proceeding from this prior art, it was an object of the present invention to significantly decrease fumaric acid deposits on plant parts and blockages, deinstallation and cleaning operations, and also shutdowns, caused thereby in the preparation of maleic anhydride with a minimum level of technical complexity and without occurrence of the above-mentioned disadvantages.

Accordingly, a process has been found for decreasing fumaric acid deposits in the preparation of maleic anhydride by heterogeneously catalyzed oxidation of a hydrocarbon selected from the group of benzene, n-butane, n-butene and 1,3-butadiene with molecular oxygen in the presence of a catalyst comprising vanadium, phosphorus and oxygen, comprising
(a) the absorption of maleic anhydride from the crude product mixture in an absorbent comprising an organic solvent in an absorption column;
(b) the desorption of the maleic anhydride from the maleic anhydride-enriched absorbent obtained in step (a) in a desorption column; and
(c) the full or partial recycling of the absorbent depleted of maleic anhydride in step (b) to step (a),
wherein
(d) the entirety or a portion of the absorbent depleted of maleic anhydride in step (b), for controlled precipitation of fumaric acid, is cooled, and/or concentrated by evaporating a portion of the absorbent, to such an extent that the difference between the concentration of fumaric acid in the recycle stream at the outlet of the desorption column c(FA, desorption column outlet), under the conditions present there, in ppm by weight, and the equilibrium concentration of fumaric acid according to the solubility curve after the cooling and/or evaporation of a portion of the absorbent c(FA, equilibrium after cooling/evaporation) in ppm by weight, is greater than or equal to 250 ppm by weight;
(e) the fumaric acid precipitated as a solid as a result of the measures from step (d) is removed completely or partly, continuously or batchwise, from the absorbent recycling; and
(f) the fumaric acid-depleted absorbent from step (e) is recycled completely or partly to step (a).

The process according to the invention significantly decreases undesired fumaric acid deposits as a result of controlled precipitation of the fumaric acid in the recycling of the absorbent through the inventive measures and the removal of precipitated fumaric acid.

DETAILED DESCRIPTION OF THE PREFERRED EMBODIMENTS

Figure 1:
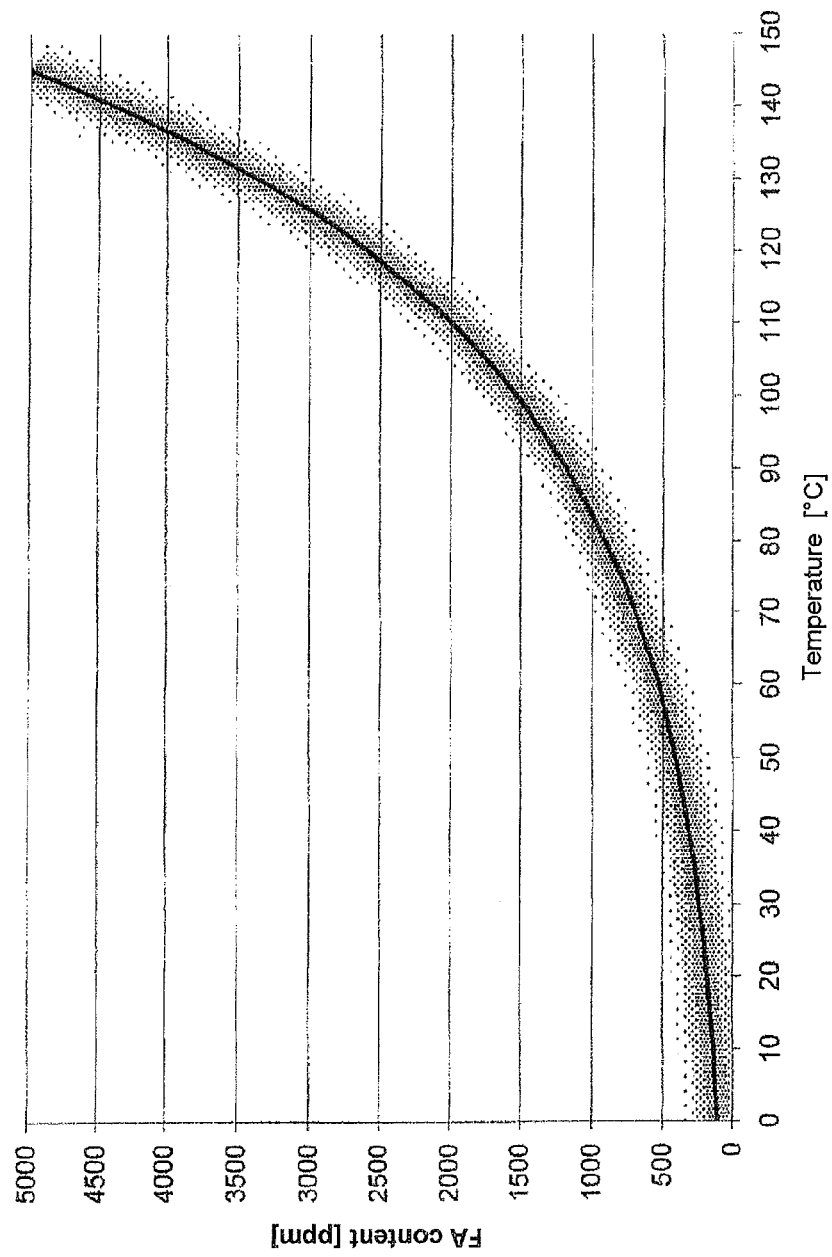
FIG. 1 shows the temperature dependence of the solubility of fumaric acid in pure di-n-butyl phthalate and in di-n-butyl phthalate-based absorbent from industrially operated plants. The area shaded gray indicates the area in which fumaric acid solubility both in pure di-n-butyl phthalate and in the studied di-n-butyl phthalate-based absorbents from industrially operated plants is present. The continuous lines correspond to the fitted curve.

It has been found in accordance with the invention, surprisingly, that the fumaric acid, under the existing conditions of heterogeneously catalyzed preparation of maleic anhydride by hydrocarbon oxidation, has an exceptionally strong tendency to the development of oversaturation. For instance, contrary to the expectation of a person skilled in the art, it does not precipitate out in accordance with the solubility curve for example in the course of cooling of the absorbent from step (b) which has been depleted of maleic anhydride, but rather itself forms a highly supersaturated solution in the presence of crystalline fumaric acid present. The supersaturation may be several hundred ppm by weight, in some cases even more than 1000 ppm by weight, and hence several times the solubility. The same also applies to the concentration by evaporation of a portion of the absorbent. This surprising behavior leads to the effect that the fumaric acid, after the prior art maleic anhydride preparation processes, precipitates out in an apparently uncontrolled manner in the absorbent recycling and downstream plant parts, gradually blocking apparatus and pipelines.

In accordance with the invention, the measures mentioned have succeeded in precipitating the fumaric acid in a controlled manner in spite of a marked tendency to supersaturation. The controlled precipitation is achieved by the measures, specified in step (d), of controlled cooling and/or controlled concentration by evaporation of a portion of the absorbent, the measures specified establishing, in a controlled manner, a difference between the concentration of fumaric acid in the recycle stream at the outlet of the desorption column c(FA, desorption column outlet) under the conditions present there in ppm by weight and the equilibrium concentration of fumaric acid according to the solubility curve after the cooling and/or evaporation of a portion of the absorbent c(FA, equilibrium after cooling/evaporation) in ppm by weight of greater than or equal to 250 ppm by weight. The upper limit of the difference thus corresponds, at a minimum equilibrium concentration of fumaric acid according to the solubility curve of 0 ppm by weight at correspondingly low temperature, to the concentration of fumaric acid in the recycle stream at the outlet of the desorption column c(FA, desorption column outlet). Advantageously, a difference of c(FA, desorption column outlet) minus c(FA, equilibrium after cooling/evaporation) of greater than or equal to 350 and preferably greater than or equal to 500 is established. in special cases, for example in the case of relatively high concentrations of fumaric acid in the absorbent of generally above 1500 ppm by weight, it is advantageous to establish a difference of c(FA, desorption column outlet) minus c(FA, equilibrium after cooling/evaporation) of more preferably greater than or equal to 700, even more preferably greater than or equal to 1000 and especially greater than or equal to 1500 ppm by weight. The difference is preferably less than or equal to 5000 and more preferably less than or equal to 3000 ppm by weight.

The concentration of fumaric acid in the recycle stream at the outlet of the desorption column c(FA, desorption column outlet) can be determined analytically in a simple manner. The analysis can be effected, for example, by means of calibrated gas chromatography. For calibration, preference is given to using an internal standard, for example diethylene glycol dimethyl ether. Before the gas chromatography analysis, the sample is generally homogenized, i.e. taken up in a solvent. One example of a solvent entirely suitable for this purpose is N,N-dimethylformamide. After the homogenization, the sample is preferably silylated with a suitable silylating agent, for example N,O-bis-(trimethylsilyl) trifluoroacetamide (BSTFA). Particularly suitable separating columns are capillary columns with 100% dimethylpolysiloxane (e.g. DB-1 from Agilent) or (14% cyanopropylphenyl)methylpolysiloxane (e.g. DB-1701 from Agilent), preferably each of length 60 m, internal diameter 0.32 mm and film thickness 1 μm.

The outlet of the desorption column is understood to mean the point at which the stream leaves the actual column. This preferably occurs via the bottom drawer. The samples for the analytical determination of concentration should also be taken therefrom.

The equilibrium concentration of fumaric acid according to the solubility curve after the cooling and/or evaporation of a portion of the absorbent c(FA, equilibrium after cooling/evaporation) can be discerned in a very simple manner from the corresponding solubility curve taking account of the temperature present. The curve of the temperature-dependant solubility of the fumaric acid in the absorbent used, which may have been partly concentrated by evaporation, (solubility curve) can be determined experimentally by the following method:

(1) The absorbent in which the temperature-dependent solubility of the fumaric acid is to be determined is cooled to 0° C. in a stirred state in a temperature-controllable stirring vessel.
(2) Then about 1% by weight of fumaric acid as a pure substance is added to the absorbent cooled to 0° C., but at least double the expected maximum solubility which is to be measured.
(3) After addition of the fumaric acid, the resulting mixture is stirred at 0° C. for 24 hours.
(4) If the solubility is to be determined at 0° C., after expiry of the 24 hours of stirring time, a sample can be taken from the stirred suspension. The sampling is effected by means of a syringe which is provided with a syringe attachment filter to retain the undissolved fumaric acid. The syringe attachment filter used is a membrane filter of pore width 0.2 micrometer. The solids-free liquid sample drawn through the filter comprises dissolved fumaric acid. Its concentration is determined analogously to the analysis method described in the determination of c(FA, desorption column outlet). The analyzed content of fumaric acid corresponds to the solubility of fumaric acid in the absorbent used at 0° C.
(5) If the solubility is to be determined at a temperature above 0° C., the suspension remaining from point (4) is heated to the desired temperature with further stirring. When establishing the new, higher temperature, the temperature of the suspension must not overshoot the desired temperature by more than 3° C. When the desired temperature has been established, the mixture is then stirred at constant temperature at least for a duration of 4 hours.
(6) After this continued stirring time, another sample is taken, as described in point (4). In each sampling, generally a new syringe attachment filter is used. When the desired temperature is more than 10° C. above room temperature, the syringe and the syringe attachment filter are appropriately preheated (for example in a heating cabinet).

(7) The filtered liquid sample is then likewise analyzed for the fumaric acid concentration by the method described in point (4). The analyzed content of fumaric acid corresponds to the solubility of fumaric acid in the absorbent used at the temperature established.

(8) When the solubility is to be determined at further, even higher temperatures, the procedure is analogous to points (5) to (7). It should be noted that, in terms of time sequence, the fumaric acid solubility should be determined only ever from the lower to the higher measurement temperature owing to the marked tendency to supersaturation.

The temperature dependence, determined in this manner, of the solubility of fumaric acid in pure di-n-butyl phthalate and in di-n-butyl phthalate-based absorbent from industrially operated plants is shown in simplified form in FIG. 1. The type and amount of the secondary components present in the di-n-butyl phthalate-based absorbents from the industrially operated plants have little influence on the solubility of the fumaric acid. Examples of secondary components caused by the industrial process include water, maleic anhydride, maleic acid, acrylic acid, methacrylic acid, acetic acid, propionic acid, phthalic anhydride and phthalic acid. The area shaded gray in FIG. 1 therefore indicates the area in which fumaric acid solubility both in pure di-n-butyl phthalate and in the studied di-n-butyl phthalate-based absorbents from industrially operated plants is present. The continuous line corresponds to the fitted curve.

It should be emphasized that, in accordance with the invention, of course, the fumaric acid solubility in the absorbent present in the particular case should always be considered. Ideally, therefore, in industrially practiced processes, the temperature dependence of the fumaric acid solubility should also be determined using an operation sample from the absorption recycling. In the case of exact, qualitative and quantitative knowledge of the secondary components, it is alternatively also possible to use a corresponding synthetic mixture.

In the concentration by evaporation of a portion of the absorbent, the entirety or a portion of the absorbent depleted in maleic anhydride in step (b) is generally fed to a column operated under reduced pressure, and the evaporated absorbent is drawn off via the top. As this is done, there is a formal rise in the concentration of dissolved fumaric acid and, when the solubility is exceeded, also in the supersaturation. In order to promote the concentration, it is generally advantageous to operate the column at a temperature above that of the absorbent recycle stream and then to cool the concentrated absorbent again. In the case of use of the very particularly preferred di-n-butyl phthalate, the concentration can particularly advantageously be performed at a pressure of from 0.001 to 0.004 MPa abs and a temperature of from 180 to 250° C.

Particularly advantageously, in step (d) of the process according to the invention, the entirety or a portion of the absorbent depleted in maleic anhydride in step (b), for controlled precipitation of the fumaric acid, is cooled to the lowest temperature in the absorbent recycling. This reduces the solubility of the fumaric acid in the absorbent and some of the fumaric acid precipitates out in solid form.

The maleic anhydride-depleted absorbent obtained in step (b) has, according to the method of removal, generally a temperature of from 100 to 300° C. It comprises generally from 0.01 to 5% by weight and preferably from 0.02 to 2% by weight of fumaric acid and generally from 0.01 to 2% by weight and preferably from 0.02 to 0.5% by weight of water. In general, the higher the content of water and the higher the temperature in the absorption in step (a) and in the removal in step (b), the higher the content of fumaric acid. In addition to the fumaric acid, the depleted absorbent further comprises, as by-products, also maleic acid, alkyl-substituted maleic acid derivatives, acrylic acid, methacrylic acid, acetic acid and propionic acid. In addition, there are further compounds which can form from the absorbent, which depend on the nature of the absorbent. When, for example, phthalic esters (phthalates) are used, as well as phthalic anhydride, phthalic acid and monoesters thereof, the esters of the aforementioned acids formed by transesterification are also possible.

The preferred cooling, specified in step (d), of the maleic anhydride-depleted absorbent obtained in step (b) can be effected in various ways. In general, cooling media which act via a heat exchange surface are used. Suitable cooling media include, for example, water, air or other gaseous or liquid streams in the context of an integrated energy system. Preference is given to cooling to the lowest temperature in the absorbent recycling. The absorbent recycling is understood to mean the entire area between the removal of the maleic anhydride in step (b) and the absorption of the maleic anhydride in step (a), around which the maleic anhydride-depleted absorbent flows. In order to achieve a particularly advantageous deposition rate of the fumaric acid in the desired local area in the absorbent recycling, the absorbent is cooled in the course of the controlled cooling preferably by from 1 to 250° C., more preferably by from 50 to 200° C. and most preferably by from 100 to 150° C. with respect to the other areas in the absorbent recycling. The temperature referred to as the lowest temperature in step (d) is preferably from 10 to 100° C., more preferably from 20 to 90° C. and most preferably from 30 to 70° C.

Preference is given to cooling the maleic anhydride-depleted absorbent to such an extent or to concentrating it by evaporating absorbent to such an extent that the amount of fumaric acid which is deposited corresponds at least to the rate of formation of fumaric acid in the overall system.

The pressure of the absorbent in the absorbent recycling is from 0.01 to 1 MPa abs, preferably from 0.09 to 0.5 MPa abs and more preferably from 0.09 to 0.3 MPa abs.

In the process according to the invention, either the entirety or a portion of the absorbent depleted in maleic anhydride in step (b) can be cooled in step (d) for controlled precipitation of the fumaric acid and/or can be concentrated by evaporating a portion of the absorbent. When only a portion is cooled for precipitation and/or concentrated by evaporating a portion of the absorbent, the rest of the stream is preferably diverted around the precipitation stage and then combined again with the fumaric acid-depleted stream or alternatively fed separately to the absorption in step (a). The precipitation from a portion may be particularly advantageous compared with a precipitation from the entire stream. For instance, owing to the lower volume flow, a smaller and generally also less expensive apparatus can be used. In addition, for example in the case of the preferred cooling with the same cooling performance, a lower temperature can be achieved and hence also a more intense depletion of the fumaric acid in this substream. Overall, this might be more advantageous in total than achieving a less intense depletion of the fumaric acid from the overall stream in a larger apparatus with the same cooling performance. The same also applies correspondingly to the concentration by evaporation of a portion of the absorbent.

Preferably, in step (d), from 5 to 100% and more preferably from 50 to 90% of the absorbent depleted in maleic anhydride in step (b) is cooled and/or concentrated by evaporating a portion of the absorbent.

As a result of the described cooling or concentration by evaporation of a portion of the absorbent, the fumaric acid partly precipitates out in solid form, the precipitation being significantly less than expected on the basis of the solubility curve owing to the marked tendency to oversaturation mentioned. As well as fumaric acid, the cooling may result in further, less soluble by-products and decomposition products precipitating out. In the case of use of phthalic esters as absorbents, these are more particularly also phthalic anhydride and phthalic acid formed therefrom. The precipitate may have crystalline or amorphous structures. This can occur as early as in the heat exchanger or downstream thereof. The precipitation can occur within the liquid phase or else as a deposit or growth on a pipe or vessel wall. Provision of an appropriately large surface area, for example through the use of structured packings or random packings, and/or of an appropriately long residence time in the vessel in which the controlled precipitation is to proceed, allows the precipitation to be made particularly effective. In this context, it is possible to draw essentially on the general technical knowledge regarding crystallization.

The fumaric acid and the other secondary components can be precipitated continuously or batchwise.

In order to further improve the precipitation of the fumaric acid from the stream which has been cooled or concentrated by evaporating a portion of the absorbent, it may be advantageous to pass the cooled or concentrated stream, before it is passed on, first through a delay vessel. This should preferably have a large inner surface area in order to further promote the deposition of the fumaric acid. Suitable apparatus for this purpose is, for example, vessels filled with random packings or structured packings. These can, if required, be removed briefly from the stream and cleaned. For cleaning, the methods described below for removing the deposited fumaric acid are useful.

In a preferred embodiment, a vessel with internals is used for the precipitation and deposition of the fumaric acid. The object of the internals is, in particular, to provide an appropriate surface area for deposition of the precipitated fumaric acid particles, i.e. those already present, and of the fumaric acid which precipitates, i.e. the fumaric acid which grows on the surface from the still dissolved state. Particular preference is therefore given to internals with a high specific surface area. The empty volume content in the vessel should preferably be from 30 to 99.5% and preferably from 90 to 99%. The specific surface area is preferably from 50 to 2000 $m^2/m^3$ and more preferably from 250 to 1200 $m^2/m^3$. For this purpose, it is possible to use, for example, commercial random packings, structured packings or wire knits made of steel, ceramic, porcelain or polymers, preferably made from stainless steel. The surface of the internals and vessel walls may be smooth or roughened. For the internals, it is also possible to use expanded metal or wire mesh. The direction of installation of the internals is as desired, but is preferably horizontal or vertical. When structured packings are used, the bend angle of the cross-channel structures should be tilted by from 10° to 80°, preferably by from 40° to 60°, against the flow direction.

When a deposition volume with internals is used, it is preferably within the apparatus in which the appropriate cooling and/or concentration by evaporation of a portion of the absorbent is effected, or downstream of this apparatus in flow direction.

The mean residence time in the vessel with internals is preferably from 0.05 to 6 hours, more preferably from 0.1 to 2 hours and most preferably from 0.2 to 1 hour. The flow rate is preferably from 0.0005 to 1.0 m/s and more preferably from 0.001 to 0.1 m/s. The vessels are operated such that adjustment of the flow rate and of the specific surface area gives rise to a fluid-dynamic state in which accumulation of precipitated, suspended and/or flocculated particles on the inner surface is established.

In a particular embodiment, internals with different specific surface area are used and are installed such that the specific surface area increases in flow direction and it increases by a factor of from 1.5 to 10, preferably from 2 to 5. In another particular embodiment, the internals are arranged such that there are free spaces for the supply or removal of liquids between the internals.

In another particular embodiment, the above-described vessel with internals may also be part of the absorption unit from step (a), to which, in step (f), the cooled and supersaturated absorbent from step (d) is recycled completely or partly to step (a). In this case, the absorption unit, which may be configured, for example, as a so-called absorption column, would preferably have internals, as described in the above paragraphs relating to the vessels with internals, in the region of the feed of the depleted absorbent.

The fumaric acid (and other by-products) precipitated as a solid as a result of the measures from step (d) is then removed completely or partly, continuously or batchwise, from the absorbent recycling in step (e). In general, in step (e), from 5 to 100%, preferably from 20 to 100% and more preferably from 50 to 100% of the fumaric acid precipitated as a solid by the measures from step (d) is removed. In steps (d) and (e), preference is given to using an apparatus from which, with constant throughput of the maleic anhydride-depleted absorbent, the deposited fumaric acid can be removed continuously or batchwise from the absorbent recycling. In the case of internals used for a specific purpose in the absorption unit from step (a), the cleaning is appropriately effected during the routine shutdowns of the plant.

The deposited fumaric acid can be removed in a wide variety of different ways, for example mechanically, physically, thermally or chemically. For example, the deposited fumaric acid can be scraped mechanically from the surface on which it has deposited. In addition, it is also possible to dissolve the deposited fumaric acid physically after emptying the absorbent from the appropriate vessel, for example in water, preferably in warm or hot water. Owing to the comparatively poor solubility in water, however, it is generally more advantageous to convert the deposited fumaric acid chemically to a readily soluble salt and to dissolve that. This is done, for example, by washing with an aqueous base, preferably sodium hydroxide solution. In addition, it is also possible to burn off the deposited fumaric acid thermally in the presence of oxygen. If the precipitated fumaric acid is present in suspended or slurried form in the absorbent, it can be removed, for example, by means of filters, decanters, cyclones or centrifuges. Particularly advantageous methods are, according to the configuration of the apparatus in which the fumaric acid is deposited, flushing out by dissolving in sodium hydroxide solution and mechanical removal by scraping.

As far as the apparatus configuration of the precipitation and deposition of the fumaric acid by the preferred cooling is concerned, essentially three fundamental principles are of particular significance, which can of course also be combined. They are explained in detail below.

A) In the first apparatus configuration, steps (d) and (e) involve using an apparatus with at least two parallel precipitation zones, from which the deposited fumaric acid, with constant throughput of the maleic anhydride-depleted absorbent through at least one of precipitation zones, can be removed batchwise from at least one other precipitation zone.

The simplest form of this is the use of exactly two parallel precipitation zones. In technical jargon, reference is also made to an NB configuration. Here, it is possible, for example, first to pass the absorbent which is to be depleted in fumaric acid only through precipitation zone A, in which it cools and the fumaric acid precipitates out. When enough fumaric acid has been deposited in precipitation zone A, it is then possible to switch to precipitation zone B and to remove the deposited fumaric acid from precipitation zone A. When enough fumaric acid has then been deposited in precipitation zone B, operation is switched back to precipitation zone A which is ready for operation.

Alternatively, the two precipitation zones A and B can be used in parallel for deposition of fumaric acid. When enough fumaric acid has then been deposited in one of the two precipitation zones, it can be removed after switching to the other precipitation zones. Subsequently, the cleaned precipitation zone can be reconnected in parallel. Advantageously, the two precipitation zones are of course operated such that their cycles are appropriately offset.

According to the above description of an NB configuration, it is of course also possible to use more than two parallel precipitation zones (referred to hereinafter as n precipitation zones). Preference is then given to using n-1 precipitation zones or all n precipitation zones in parallel for deposition of fumaric acid. When enough fumaric acid has been deposited in one of the precipitation zones used, it can be disconnected for the removal thereof. If an unused precipitation zone ready for operation is present, this can then be connected. After the cleaning of the disconnected precipitation zone, it is then either reconnected immediately or kept in a waiting position until another precipitation zone is disconnected. Advantageously, even in the case of more than two precipitation zones, they are of course operated such that their cycles are correspondingly offset.

The particular advantage of the first apparatus configuration is that the process can be operated without interruption of the controlled precipitation of the fumaric acid. A disadvantage is that at least two parallel precipitation zones are required. However, this disadvantage becomes virtually meaningless when parallel units are already present or are to be used in any case for plant technology reasons. A preferred embodiment for this purpose is the use of an air cooler with a plurality of parallel registers.

B) In the second apparatus configuration, steps (d) and (e) involve using an apparatus with a bypass, from which the deposited fumaric acid, with constant throughput of the maleic anhydride-depleted absorbent through the bypass, can be removed batchwise from the apparatus.

In this variant, the absorbent which is to be depleted in fumaric acid is passed through the precipitation zone of the apparatus. When enough fumaric acid has been deposited therein, the apparatus is disconnected for cleaning and the absorbent is conducted past this apparatus via the bypass. Subsequently, the cleaned apparatus is reconnected.

Alternatively, it is also possible always to conduct a portion of the absorbent to be depleted in fumaric acid through the bypass. The apparatus intended for precipitation is thus loaded only with a relatively small liquid stream and can therefore also be designed with smaller dimensions. With the same cooling performance, owing to the smaller absorbent stream, a lower temperature is achievable, which leads to a higher relative deposition of fumaric acid. When the apparatus has to be cleaned, the entire stream is briefly conducted through the bypass.

In a particular design, the precipitation zone can also be integrated into one of the apparatuses present, preferably the apparatus for the maleic anhydride absorption.

The particular advantage of the second apparatus configuration is that only one apparatus with a precipitation zone is required. However, a disadvantage of this is that no controlled precipitation of the fumaric acid can be effected during the cleaning of the apparatus. A rapid and uncomplicated cleaning procedure of the disconnected apparatus, however, can significantly reduce this disadvantage.

C) In the third apparatus configuration, steps (d) and (e) involving using an apparatus from which, with constant throughput of the maleic anhydride-depleted absorbent, the deposited fumaric acid can be removed continuously or batchwise from the absorbent recycling with constant operation of the precipitation zone.

This includes, for example, apparatus which scrape off and remove fumaric acid deposited on a surface in a continuous or batchwise manner with constant operation, as is the case, for example, for the known, commercial, cooling and rotary crystallizers. These also include apparatus in which the precipitated fumaric acid is obtained as a suspension or slurry, from which it can then be removed by mechanical and physical methods, for example by means of filters, decanters, cyclones or centrifuges.

The particular advantage of the third apparatus configuration is that only one apparatus with one precipitation zone is required and it can be operated continuously without disconnection and separate cleaning. A disadvantage is, however, the somewhat increased apparatus complexity as a result of the use of special apparatus, for example a crystallizer, filter, decanter, cyclone or a centrifuge.

In the selection of the apparatus configuration of the precipitation of fumaric acid, it is particularly advantageous to weigh the advantages and disadvantages mentioned against one another taking account of the overall system.

The fumaric acid-depleted absorbent from step (d) is conducted, in step (f), completely or partly back to step (a). in general, in step (f), from 10 to 100%, preferably from 50 to 100% and more preferably from 90 to 100% of the fumaric acid-depleted absorbent from step (d) is recycled to step (a). With regard to the precipitation of fumaric acid, it can generally be recycled to step (a) without downstream heating, since the fumaric acid which is precipitable within the technically relevant time scale has generally already precipitated out owing to the oversaturation. If required, for example to achieve the desired entrance temperature for the absorption column, however, there is no reason to avoid heating.

The maleic anhydride-comprising crude product mixture to be used in step (a) in the process according to the invention can be obtained in an upstream stage by heterogeneously catalyzed oxidation of a hydrocarbon selected from the group of benzene, n-butane, n-butene and 1,3-butadiene with molecular oxygen in the presence of a catalyst comprising vanadium, phosphorus and oxygen. In general, the heterogeneously catalyzed oxidation is performed in a tube bundle reactor. Processes for oxidizing n-butane are described, for example, in Ullmann's Encyclopedia of Industrial Chemistry, 2005 Wiley-VCH Verlag GmbH & Co KGaA, Weinheim, "Maleic and Fumaric Acids-Maleic Anhydride".

The crude product mixture thus obtained is then absorbed in step (a) in a suitable organic solvent as an absorbent.

The maleic anhydride-comprising crude product mixture can be contacted with the solvent (absorbent) in various ways, preferably at pressures of from 0.08 to 1 MPa abs and a temperature of from 50 to 300° C.: (i) by introducing the gas stream into the solvent (for example via gas introduction nozzles or sparging rings), (ii) by spraying the solvent into the gas stream or (iii) by countercurrent contact between the gas stream flowing upward and the solvent flowing downward in a column with trays or packings. In all three variants, the apparatus known to those skilled in the art for gas absorption can be used. In the selection of the solvent (absorbent) to be used, it should be ensured that it does not react with the reactant, the maleic anhydride used. In addition, owing to the subsequent removal of the maleic anhydride from the absorbent, a corresponding difference in the boiling points of the absorbent and of the maleic anhydride should be ensured. The organic solvent, based on atmospheric pressure, preferably has a boiling point at least 30° C. higher than that of the maleic anhydride.

Suitable absorbents are, for example, phosphoric esters (e.g. tricresyl phosphate), maleic esters (e.g. dibutyl maleate, butyl maleate), high molecular weight waxes, aromatic hydrocarbons having a molecular weight between 150 and 400 g/mol and a boiling point above 140° C. (e.g. dibenzylbenzene), phthalic esters (e.g. alkyl phthalates and dialkyl phthalates with $C_1$-$C_{18}$-alkyl groups, for example dimethyl phthalate, diethyl phthalate, di-n-propyl phthalate, diisopropyl phthalate, di-n-butyl phthalate, diundecyl phthalate, methyl phthalate, ethyl phthalate, n-propyl phthalate, isopropyl phthalate, butyl phthalate, undecyl phthalate), di-$C_1$-$C_4$-alkyl esters of other aromatic and aliphatic dicarboxylic acids (e.g. dimethyl-2,3-naphthalenedicarboxylic acid dimethyl ester, dimethyl-1,4-cyclohexanedicarboxylic acid dimethyl ester), $C_1$-$C_4$-alkyl esters of other aromatic and aliphatic dicarboxylic acids (e.g. dimethyl 2,3-naphthalenedicarboxylate, dimethyl 1,4-cyclohexanedicarboxylate of long-chain fatty acids having, for example, from 14 to 30 carbon atoms), high-boiling ethers (e.g. dimethyl ethers of polyethylene glycol or tetraethylene glycol dimethyl ether).

Preference is given to using phthalic esters, particular preference to using di($C_1$- to $C_{12}$-alkyl) phthalate and very particular preference to using di-n-butyl phthalate.

The solution which results from the absorption in step (a) generally has a content of maleic anhydride of from about 5 to 400 g/l.

The offgas stream which remains after the absorption in step (a) comprises, as well as water, principally the by-products of the preceding oxidation, for instance carbon monoxide, carbon dioxide, unconverted starting hydrocarbons, and acetic acid and acrylic acid. The offgas stream is substantially free of maleic anhydride.

Subsequently, in step (b), the maleic anhydride is removed from the maleic anhydride-enriched absorbent obtained in step (a). The removal is effected preferably by stripping with a suitable gas, especially hydrogen, or by distillation.

Stripping with hydrogen is advantageous in particular when the maleic anhydride is subsequently to be hydrogenated to tetrahydrofuran, 1,4-butanediol and/or gamma-butyrolactone. In this case, the stripping is effected preferably at a temperature of from 100 to 250° C. and a pressure of from 0.08 to 3 MPa abs, the pressure preferably being a maximum of 10% above the pressure of the subsequent hydrogenation. In the stripping column, a temperature profile is observed which arises from the boiling points of maleic anhydride at the top and of the virtually maleic anhydride-free absorbent in the bottom of the column at the particular column pressure and the established dilution with carrier gas (in the first case with hydrogen). In order to prevent losses of absorbent, rectifying internals may be present above the feed of the maleic anhydride-enriched absorbent.

Alternatively to the hydrogen stripping, the maleic anhydride dissolved in the absorbent can also be removed in a distillation unit at pressures of generally from 0.001 to 0.5 MPa abs and temperatures of from 65 to 300° C. The distillation can be carried out in one stage or a plurality of stages, for example in separating apparatus with one stage or a plurality of stages, for example columns with a plurality of separating stages, for example rectification columns, columns with random packing, bubble-cap tray columns or columns with structured packing.

In step (c), preferably from 50 to 100% and more preferably from 90 to 100% of the absorbent depleted in maleic anhydride in step (b) is recycled to step (a).

In a basic procedure, the absorbent which has been freed of maleic anhydride is first degassed and subsequently cooled by means of an air cooler to a temperature slightly above that required in the subsequent process stage of absorption. This temperature is selected such that there is only just no deposition of the fumaric acid enriched in the absorbent. In a subsequent cooling stage, which may be configured as an air or water cooler, the absorbent is then cooled, with deposition of fumaric acid, to a temperature which leads to a difference between the concentration of fumaric acid in the recycle stream at the outlet of the desorption column c(FA, desorption column outlet), under the conditions existing there, in ppm by weight, and the equilibrium concentration of fumaric acid according to the solubility curve after the cooling c(FA, equilibrium after cooling) in ppm by weight, of greater than or equal to 250 ppm by weight. This allows the precipitation of fumaric acid to be controlled such that only this apparatus has to be cleaned at regular intervals. Shutting down the entire plant can be avoided by configuring this cooler in an NB system.

When only a substream is passed through the deposition cooler, this stream can be reduced further. Moreover, for the short cleaning interval, it is possible to simply bypass the crystallization stage and thus avoid an A/B configuration. Here too, the cooler itself may be configured as a singular cooler or, much more efficiently, as a connection of cross flow cooler and deposition cooler as described in the above paragraph.

In existing systems, in which the main cooler consists of a plurality of parallel strands, as is the case for air coolers in the form of individual registers, a deposition of the fumaric acid which is likewise very simple and efficient can be achieved by partly throttling individual registers: the throttled register cools significantly more rapidly and deposits the fumaric acid very effectively, while the warmer main register remains substantially free of deposits. Here too, the sacrificial register, after partitioning off with gate valves in the incoming and outgoing lines, can be cleaned during the operation of the main register without interruption to the process.

The process according to the invention enables the significant decrease of fumaric acid deposits on plant parts and of blockages, deinstallation and cleaning operations, and also shutdowns, caused as a result in the preparation of maleic anhydride, the process being performable with a relatively low level of technical complexity and the known disadvantages from the prior art being avoided.

EXAMPLES

Example 1 (Inventive)

Figure 2:
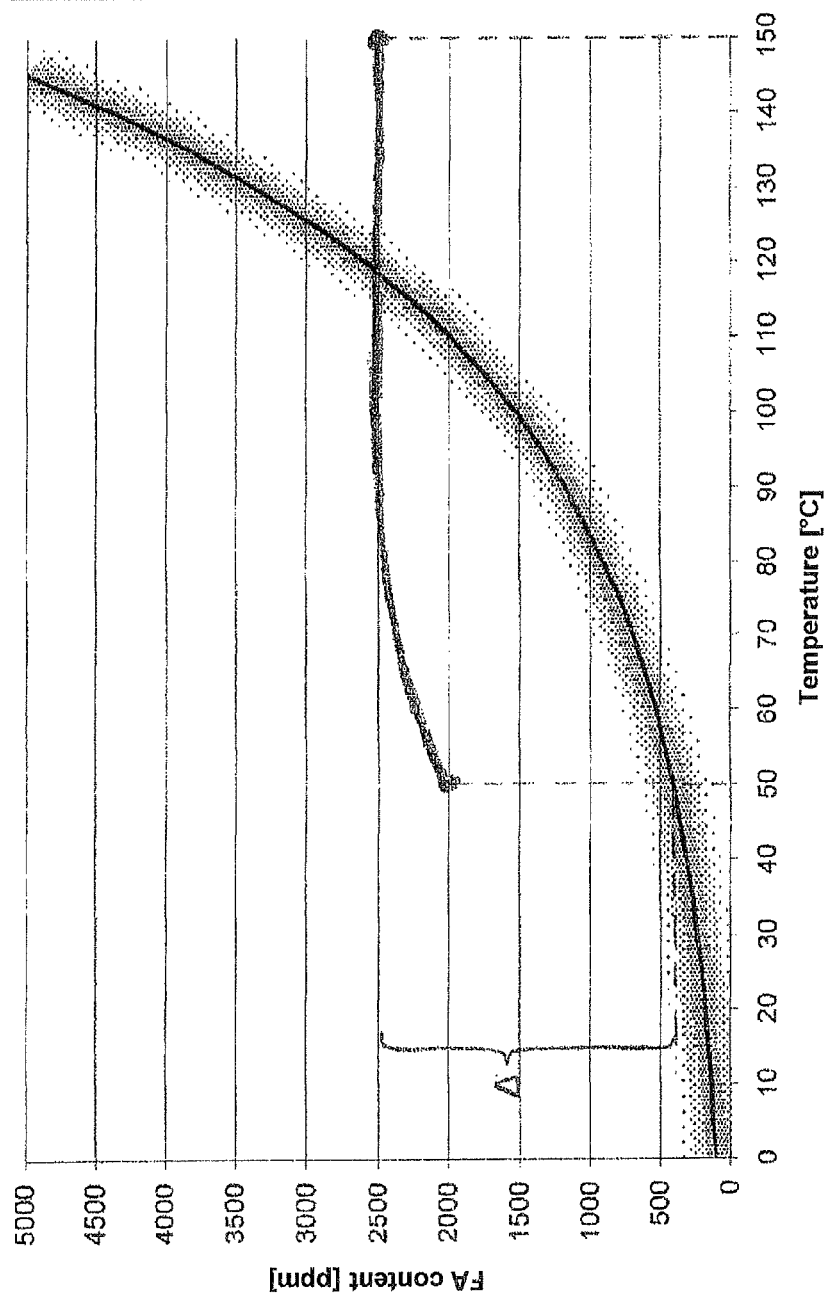
FIG. 2 is the plot of the fumaric acid concentrations in a stream conducted through four registers, as described in Example 1.

In a theoretical example, the maleic anhydride-depleted di-n-butyl phthalate is withdrawn from the bottom of the desorption column at 150° C. The concentration of fumaric acid is 2500 ppm by weight. The recycle stream is passed completely into an air cooler with ten identical registers. 50% of the stream at 150° C. is passed through two registers and cooled therein to 100° C. The other 50% is passed through four registers and cooled to 50° C. A portion of the fumaric acid is deposited in the four registers and the concentration of dissolved fumaric acid (determined by means of sampling using the 0.2 micrometer membrane filter already described) falls to 2000 ppm by weight. Subsequently, the two streams are combined to one stream at 75° C. comprising 2250 ppm by weight of dissolved fumaric acid and fed to the absorption column. The plot of the fumaric acid concentration in the stream conducted through the four registers is shown schematically in FIG. 2. The equilibrium concentration of fumaric acid according to the solubility curve after cooling to 50° C. c(FA, equilibrium after cooling/evaporation) is about 400 ppm by weight. The difference c(FA, desorption column outlet) minus c(FA, equilibrium after cooling/evaporation) is therefore about 2100 ppm by weight.

Once the flow resistance has increased noticeably owing to the fumaric acid deposits in the four registers used for cooling to 50° C., the flow is switched to the other four registers with continuing operation and the registers covered with fumaric acid are cleaned with aqueous sodium hydroxide solution or hot water.

Experimental Procedure for Examples 2 to 5

Figure 3:
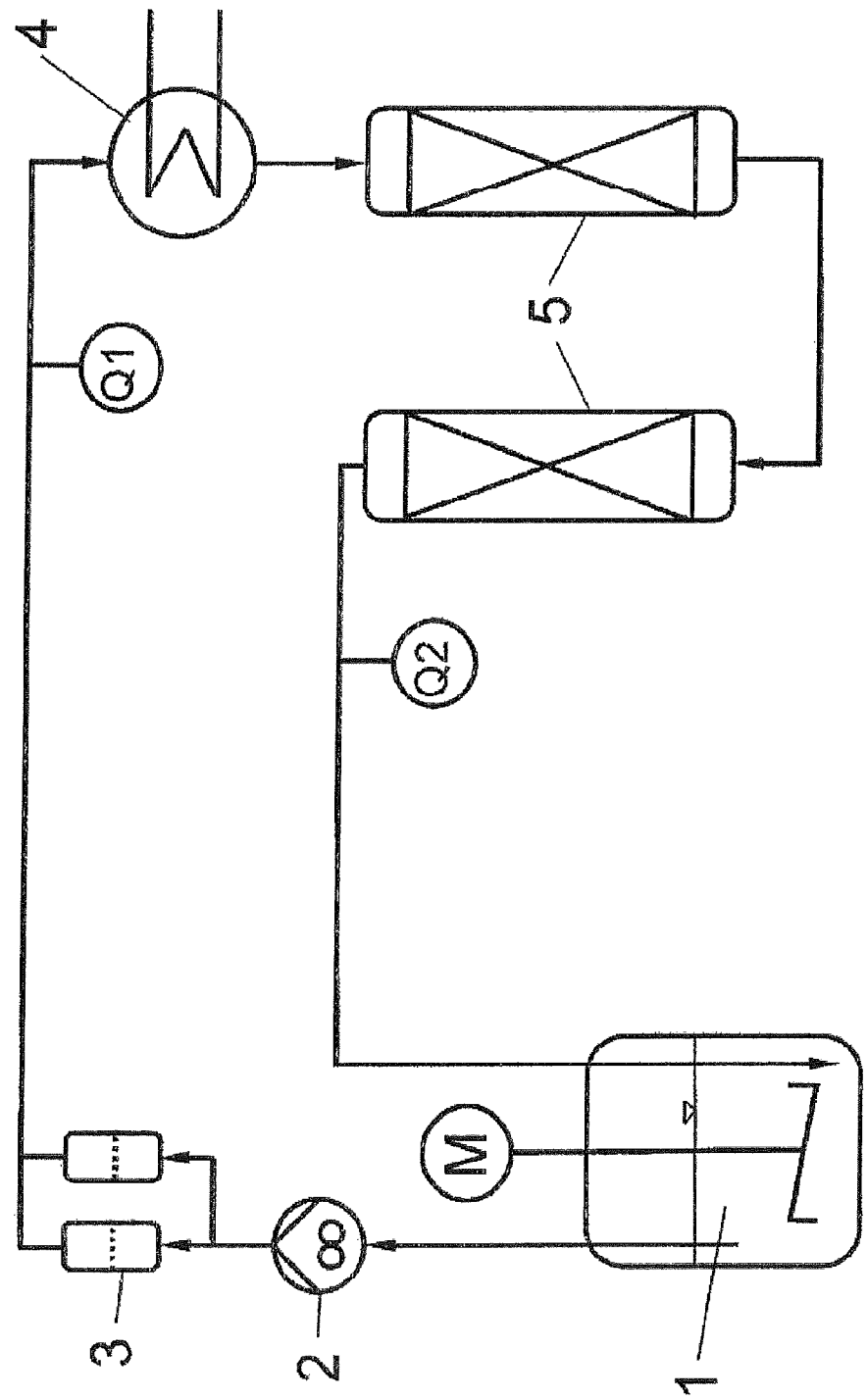
FIG. 3 is a simplified diagram of a test plant.

For the performance of experimental examples 2 to 5, a test plant on the laboratory scale was used. FIG. 3 shows a simplified diagram of this test plant. In a stirred vessel (1) which had a capacity of 8 l, dibutyl phthalate was enriched with fumaric acid at a temperature of 95° C. to 120° C., cooled to from 30° C. to 70° C. in a cooler (4) via filters (3) with a pump (2), and passed through a delay zone (5). The delay zone consisted of 2 glass tubes with an internal diameter of 30 mm. The glass tubes were each filled with packings (Kühni Rombopak 9M), packing height 2×1 m. The stirred vessels and glass tubes had a jacketed design for temperature control. Downstream of the delay zone, the solution was fed back to the stirred vessel and enriched with fumaric acid. In the delay zone, some of the fumaric acid separated out on establishment of an inventive oversaturation. The sampling to determine the fumaric acid concentration was effected upstream of the cooler (Q1) and downstream of the delay zone (Q2). The amount of fumaric acid present in the stirred vessel was always such that a sediment remained.

Example 2 (Inventive)

The experiment was carried out with a mixture of dibutyl phthalate and fumaric acid. The saturation concentration of fumaric acid in the solution at 50° C. was 250 ppm by weight. In the test plant, a volume flow rate of 15.7 l/h was established, which corresponds to a residence time of 0.09 h or a flow rate of 0.00617 m/s in the delay zone. In the stirred vessel, a temperature of 100° C. was established, and 50° C. at the outlet of the cooler. Upstream of the cooler, a fumaric acid concentration of 657 ppm by weight was measured. The concentration difference c(upstream of cooler)−c(saturation at 50° C. downstream of cooler) was thus 407 ppm by weight. The fumaric acid concentration downstream of the delay zone was 359 ppm by weight. Thus, 298 ppm by weight were separated out in the delay zone.

Example 3 (Comparative Example)

The experiment was carried out with a mixture of dibutyl phthalate and fumaric acid. The saturation concentration of fumaric acid in the solution at 50° C. was 250 ppm by weight. In the test plant, a volume flow rate of 15.7 l/h was established, which corresponds to a residence time of 0.09 h or a flow rate of 0.00617 m/s in the delay zone. In the stirred vessel, a temperature of 115° C. was established, and 50° C. at the outlet of the cooler. Upstream of the cooler, a fumaric acid concentration of 435 ppm by weight was measured. The concentration difference c(upstream of cooler)−c(saturation at 50° C. downstream of cooler) was thus 185 ppm by weight. The fumaric acid concentration downstream of the delay zone was determined to be 416 ppm by weight.

Taking account of measurement and analysis accuracy, this example shows that there is no deposition of fumaric acid in the delay zone under the conditions established.

Example 4 (Inventive)

The experiment was carried out with a solution from an industrially operated plant for preparation of maleic anhydride (dibutyl phthalate concentration >98.5% by weight). The saturation concentration of fumaric acid in the solution at 30° C. was 250 ppm by weight. In the test plant, a volume flow rate of 3.5 l/h was established, which corresponds to a residence time of 0.404 h or a flow rate of 0.00138 m/s in the delay zone. In the stirred vessel, a temperature of 120° C. was established, and 30° C. at the outlet of the cooler. Upstream of the cooler, a fumaric acid concentration of 1043 ppm by weight was measured. The concentration difference c(upstream of cooler)−c(saturation at 30° C. downstream of cooler) was thus 793 ppm by weight. The fumaric acid concentration downstream of the delay zone was 634 ppm by weight. Thus, 409 ppm by weight were separated out in the delay zone.

Example 5 (Inventive)

The experiment was carried out with a solution from an industrially operated plant for preparation of maleic anhydride (dibutyl phthalate concentration >98.5% by weight). The saturation concentration of fumaric acid in the solution at 50° C. was 400 ppm by weight. In the test plant, a volume flow rate of 3.5 l/h was established, which corresponds to a residence time of 0.404 h or a flow rate of 0.00138 m/s in the delay zone. In the stirred vessel, a temperature of 95° C. was established, and 50° C. at the outlet of the cooler. Upstream of the cooler, a fumaric acid concentration of 1130 ppm by weight was measured. The concentration difference c(upstream of cooler)−c(saturation at 50° C. downstream of cooler) was thus 730 ppm by weight. The fumaric acid concentration downstream of the delay zone was 1059 ppm by weight. Thus, 71 ppm by weight were separated out in the delay zone.

The invention claimed is:
1. A process for decreasing fumaric acid deposits in the preparation of maleic anhydride by heterogeneously catalyzed oxidation of a hydrocarbon selected from the group of benzene, n-butane, n-butene and 1,3-butadiene with molecular oxygen in the presence of a catalyst comprising vanadium, phosphorus and oxygen, comprising

(a) the absorption of maleic anhydride from the crude product mixture in an absorbent comprising an organic solvent in an absorption column;
(b) the desorption of the maleic anhydride from the maleic anhydride-enriched absorbent obtained in step (a) in a desorption column; and
(c) the full or partial recycling of the absorbent depleted of maleic anhydride in step (b) to step (a), wherein (d) the entirety or a portion of the absorbent depleted of maleic anhydride in step (b), for controlled precipitation of fumaric acid, is cooled from a temperature in the range from 100 to 150° C. to a temperature in the range from 30 to 70° C., and/or concentrated by evaporating a portion of the absorbent, to such an extent that the difference between the concentration of fumaric acid in the recycle stream at the outlet of the desorption column c(fumaric acid, desorption column outlet), under the conditions present there, in ppm by weight, and the equilibrium concentration of fumaric acid according to the solubility curve after the cooling and/or evaporation of a portion of the absorbent c(fumaric acid, equilibrium after cooling/evaporation) in ppm by weight, is greater than or equal to 250 ppm by weight and a vessel with internals is used for the precipitation and deposition of the fumaric acid, the mean residence time in the vessel with internals being from 0.05 to 6 hours;
(e) the fumaric acid precipitated as a solid as a result of the measures from step (d) is removed completely or partly, continuously or batchwise, from the absorbent recycling; and
(f) the fumaric acid-depleted absorbent from step (e) is recycled completely or partly to step (a).

2. The process according to claim 1, wherein, in step (d), the average residence time in the vessel with internals is at least 0.1 hour.

3. The process according to claim 1, wherein, in step (d), the entirety or a portion of the absorbent depleted in maleic anhydride in step (b), for controlled precipitation of fumaric acid, is cooled, and/or concentrated by evaporating a portion of the absorbent, to such an extent that the difference c(fumaric acid, desorption column outlet) minus c(fumaric acid, equilibrium after cooling/evaporation) is greater than or equal to 500 ppm by weight.

4. The process according to claim 1, wherein step (d) involves cooling to the lowest temperature within the entire absorbent recycling system.

5. The process according to claim 1, wherein steps (d) and (e) involve using an apparatus from which, with constant throughput of maleic anhydride-depleted absorbent, the fumaric acid deposited can be removed continuously or batchwise from the absorbent recycling system.

6. The process according to claim 1, wherein steps (d) and (e) involve using an apparatus with at least two parallel precipitation zones, from which the deposited fumaric acid, with constant throughput of the maleic anhydride-depleted absorbent through at least one of precipitation zones, can be removed batchwise from at least one other precipitation zone.

7. The process according to claim 1, wherein steps (d) and (e) involve using an apparatus with a bypass, from which the deposited fumaric acid, with constant throughput of the maleic anhydride-depleted absorbent through the bypass, can be removed batchwise from the apparatus.

8. The process according to claim 1, wherein step (d) involves cooling from 5 to 100% of the absorbent depleted in maleic anhydride in step (b) and/or concentrating it by evaporating a portion of the absorbent.

9. The process according to claim 1, wherein step (f) involves recycling from 50 to 100% of the fumaric acid-depleted absorbent from step (d) to step (a).

10. The process according to claim 1, wherein the organic solvent to be used in step (a) to absorb maleic anhydride from the crude product mixture is a di-($C_1$- to $C_{12}$-alkyl) phthalate.

11. The process according to claim 1, wherein step (c) involves recycling from 50 to 100% of the absorbent depleted in maleic anhydride in step (b) to step (a).

* * * * *